(12) United States Patent
Godfrey et al.

(10) Patent No.: US 8,062,264 B2
(45) Date of Patent: *Nov. 22, 2011

(54) FLUID DISPENSING DEVICE (75) Inventors: James William Godfrey, Ware (GB); Mark Graham Hedley, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/911,060

(22) PCT Filed: Apr. 5, 2006

(86) PCT No.: PCT/GB2006/001264
§ 371 (c)(1),
(2), (4) Date: May 27, 2008

(87) PCT Pub. No.: WO2006/109021
PCT Pub. Date: Oct. 19, 2006

(65) Prior Publication Data
US 2008/0249459 A1 Oct. 9, 2008

(30) Foreign Application Priority Data
Apr. 9, 2005 (GB) .................................. 0507224.4

(51) Int. Cl.
*A61M 5/00* (2006.01)
*A61M 11/00* (2006.01)
*B67D 7/84* (2010.01)
(52) U.S. Cl. .................... 604/181; 128/200.14; 222/162
(58) Field of Classification Search .............. 604/93.01, 604/94.01, 890.1–892.1, 181, 183–187, 207, 604/212–217, 246–250; 222/162; 128/200.14, 128/200.22, 200.23
See application file for complete search history.

(56) References Cited

U.S. PATENT DOCUMENTS
2,602,569 A 7/1952 Ryan
(Continued)

FOREIGN PATENT DOCUMENTS
DE 2633901 A1 2/1977
(Continued)

OTHER PUBLICATIONS
Contiguous. (2009). In Merriam-Webster Online Dictionary. Retrieved Jul. 28, 2009, from http://www.merriam-webster.com/dictionary/contiguous.*
(Continued)

*Primary Examiner* — Nicholas D Lucchesi
*Assistant Examiner* — Nathan R Price
(74) *Attorney, Agent, or Firm* — James P. Riek (57) ABSTRACT

A fluid dispensing device for dispensing a fluid product having a dispensing member mounted for movement along an axis X-X from a first position to a second position which causes a dose of a fluid product to be dispensed, and a finger-operable actuator member movable in an actuating direction generally transverse to the axis to cause at least one cam surface thereof to cam the dispensing member from the first position to the second position. The at least one cam surface has a commitment section, oriented at a first angle to the axis selected such that a minimum actuating force is required to be applied to the actuator member to cause the at least one cam follower surface to ride over the commitment section onto the drive section. The commitment section of the cam surface is arcuate.

20 Claims, 9 Drawing Sheets

U.S. PATENT DOCUMENTS

| | | | |
|---|---|---|---|
| 2,673,008 A | 3/1954 | Ryan | |
| 2,904,223 A | 9/1959 | Ryan | |
| 3,237,809 A | 3/1966 | Daragan et al. | |
| 3,272,391 A | 9/1966 | Meshberg | |
| 3,405,843 A | 10/1968 | Watson | |
| 3,516,424 A | 6/1970 | Eagle | |
| 4,083,476 A | 4/1978 | Schwartz et al. | |
| 4,111,338 A | 9/1978 | Cheng et al. | |
| 4,132,359 A | 1/1979 | Nozawa | |
| 4,155,487 A * | 5/1979 | Blake | 222/207 |
| 4,185,776 A | 1/1980 | Nozawa | |
| 4,223,812 A | 9/1980 | van Lit | |
| 4,402,430 A | 9/1983 | Fox et al. | |
| 4,648,393 A | 3/1987 | Landis et al. | |
| 4,678,106 A | 7/1987 | Newell et al. | |
| 4,765,515 A | 8/1988 | Lippman | |
| 4,771,769 A | 9/1988 | Hegemann et al. | |
| 4,807,786 A | 2/1989 | Gueret | |
| 4,860,738 A | 8/1989 | Hegemann et al. | |
| 4,921,142 A | 5/1990 | Graf et al. | |
| 4,944,429 A | 7/1990 | Bishop et al. | |
| 4,946,069 A | 8/1990 | Fuchs | |
| 5,062,549 A | 11/1991 | Smith et al. | |
| 5,064,122 A | 11/1991 | Kamishita et al. | |
| 5,190,029 A | 3/1993 | Bryon et al. | |
| 5,273,189 A | 12/1993 | Jouillat et al. | |
| 5,487,489 A | 1/1996 | Weiss et al. | |
| 5,568,884 A | 10/1996 | Bruna | |
| 5,899,365 A | 5/1999 | Eichler et al. | |
| 6,152,330 A | 11/2000 | Polan | |
| 6,189,739 B1 | 2/2001 | Von Schuckmann | |
| 6,237,812 B1 | 5/2001 | Fukada | |
| 6,257,457 B1 | 7/2001 | Oechsel | |
| 6,261,274 B1 | 7/2001 | Arghyris et al. | |
| 6,302,101 B1 | 10/2001 | Py | |
| 6,305,371 B1 | 10/2001 | Frid et al. | |
| 6,315,165 B1 | 11/2001 | Regan | |
| 6,338,422 B1 | 1/2002 | DeJonge | |
| 6,364,166 B1 | 4/2002 | Ritsche et al. | |
| 6,382,205 B1 | 5/2002 | Weinstein et al. | |
| 6,382,465 B1 | 5/2002 | Greiner-Perth | |
| 6,419,124 B1 | 7/2002 | Hennemann et al. | |
| 6,484,715 B1 | 11/2002 | Ritsche et al. | |
| 6,527,144 B2 | 3/2003 | Ritsche et al. | |
| 6,568,389 B1 | 5/2003 | Rand et al. | |
| 6,578,741 B2 | 6/2003 | Ritsche et al. | |
| 6,644,305 B2 | 11/2003 | MacRae et al. | |
| 6,745,760 B2 | 6/2004 | Grychowski et al. | |
| 6,750,210 B2 | 6/2004 | Biggadike | |
| 6,860,411 B2 | 3/2005 | Stradella | |
| 7,108,159 B2 | 9/2006 | Stradella | |
| 7,353,971 B2 | 4/2008 | Stradella | |
| 2001/0013343 A1 | 8/2001 | Andersson | |
| 2002/0008122 A1 | 1/2002 | Ritsche et al. | |
| 2002/0011530 A1 | 1/2002 | Fuchs | |
| 2002/0117513 A1 | 8/2002 | Helmlinger | |
| 2002/0170923 A1 | 11/2002 | Vatman | |
| 2002/0170928 A1 | 11/2002 | Grychowski et al. | |
| 2003/0052196 A1 | 3/2003 | Fuchs | |
| 2003/0100867 A1 | 5/2003 | Fuchs | |
| 2004/0245291 A1 | 12/2004 | Simon et al. | |
| 2005/0040188 A1 * | 2/2005 | Herry et al. | 222/321.6 |
| 2005/0072861 A1 | 4/2005 | Petit | |
| 2005/0098175 A1 | 5/2005 | Stradella | |
| 2005/0211241 A1 | 9/2005 | Anderson et al. | |
| 2005/0224525 A1 | 10/2005 | Davies | |
| 2005/0234402 A1 | 10/2005 | Collins et al. | |
| 2005/0258191 A1 | 11/2005 | Davies | |
| 2006/0108378 A1 | 5/2006 | Cohen et al. | |
| 2007/0056585 A1 | 3/2007 | Davis et al. | |
| 2007/0095853 A1 | 5/2007 | Bonney et al. | |
| 2007/0131717 A1 | 6/2007 | Davies et al. | |
| 2007/0138207 A1 | 6/2007 | Bonney et al. | |

FOREIGN PATENT DOCUMENTS

| | | |
|---|---|---|
| DE | 19610456 A | 9/1997 |
| EP | 0412524 A1 | 2/1991 |
| EP | 0461277 B1 | 12/1991 |
| EP | 1129786 A2 | 9/2001 |
| FR | 2570000 A1 | 3/1986 |
| FR | 2671294 A1 | 7/1992 |
| FR | 2807954 A | 10/2001 |
| FR | 2812826 A | 2/2002 |
| GB | 173123 | 12/1921 |
| GB | 0659132 | 10/1951 |
| GB | 0906837 A | 9/1962 |
| GB | 1097254 A | 1/1968 |
| GB | 2251898 A | 7/1992 |
| JP | 04057264 U | 2/1992 |
| JP | 09048455 A | 2/1997 |
| JP | 09225363 A | 9/1997 |
| JP | 09313998 A | 12/1997 |
| JP | 10001155 | 6/1998 |
| JP | 10179739 A | 7/1998 |
| JP | 2000355382 | 12/2000 |
| WO | 9405593 A1 | 3/1994 |
| WO | 9411115 A1 | 5/1994 |
| WO | 9901229 A1 | 1/1999 |
| WO | 9938555 A1 | 8/1999 |
| WO | 9949984 A1 | 10/1999 |
| WO | 0007740 A1 | 2/2000 |
| WO | 0018458 A1 | 4/2000 |
| WO | 0136018 A2 | 5/2001 |
| WO | 0220168 A1 | 3/2002 |
| WO | 0220370 A1 | 3/2002 |
| WO | 0244056 A1 | 6/2002 |
| WO | 0249698 A1 | 6/2002 |
| WO | 02053294 A1 | 7/2002 |
| WO | 03020350 A1 | 3/2003 |
| WO | 03026803 A1 | 4/2003 |
| WO | 03026804 A1 | 4/2003 |
| WO | 03026805 A1 | 4/2003 |
| WO | 03029105 A1 | 4/2003 |
| WO | 03041865 A1 | 5/2003 |
| WO | 03061843 A1 | 7/2003 |
| WO | 03095006 A2 | 11/2003 |
| WO | 03095007 A2 | 11/2003 |
| WO | 2004/013009 | 2/2004 |
| WO | 2004012799 A2 | 2/2004 |
| WO | 2004080606 A1 | 9/2004 |
| WO | 2005028007 A1 | 3/2005 |
| WO | 2005044354 A1 | 5/2005 |
| WO | 2005087615 A1 | 9/2005 |
| WO | 2006109021 A1 | 10/2006 |

OTHER PUBLICATIONS

U.S. Appl. No. 10/513,201—Office Action dated Aug. 18, 2008.
U.S. Appl. No. 10/513,201—Final Office Action dated May 27, 2009.
U.S. Appl. No. 10/523,163—Final Office Action dated May 29, 2009.
U.S. Appl. No. 10/523,163—Notice of Allowance dated Jul. 28, 2008.
U.S. Appl. No. 10/523,163—Office Action dated Nov. 17, 2008.
U.S. Appl. No. 10/523,163—Office Action dated Jun. 25, 2007.
U.S. Appl. No. 10/513,201—Reply to the Final Office Action dated May 27, 2009.
U.S. Appl. No. 10/577,977—Office Action dated Sep. 18, 2009.
U.S. Appl. No. 10/577,977—Reply to the Office Action dated Sep. 18, 2009.
U.S. Appl. No. 10/513,201 filed May 7, 2003.
Amendment filed Feb. 18, 2009 in response to Non-Final Rejection issued Aug. 18, 2008 for U.S. Appl. No. 10/513,201.
Request for Continued Examination (RCE) with Amendment and Terminal Disclaimer filed Aug. 27, 2009 for U.S. Appl. No. 10/513,201.
Terminal Disclaimer approved by USPTO on Sep. 27, 2009 for U.S. Appl. No. 10/513,201.
Non-Final Rejection issued Mar. 18, 2010 for U.S. Appl. No. 10/513,201.
Amendment filed Jun. 17, 2010 in response to Non-Final Rejection issued Mar. 18, 2010 for U.S. Appl. No. 10/513,201.
Notice of Allowance issued Sep. 1, 2010 for U.S. Appl. No. 10/513,201.

Request for Continued Examination (RCE) with Amendment and IDS filed Dec. 1, 2010 for U.S. Appl. No. 10/513,201.
Notice of Allowance issued Dec. 17, 2010 for U.S. Appl. No. 10/513,201.
Request for Continued Examination (RCE) with IDS filed Mar. 17, 2011 for U.S. Appl. No. 10/513,201.
Notice of Allowance issued Apr. 4, 2011 for U.S. Appl. No. 10/513,201.
U.S. Appl. No. 10/523,163 filed Jul. 30, 2003.
Amendment filed Dec. 20, 2007 in response to Non-Final Rejection issued Jun. 25, 2007 for U.S. Appl. No. 10/523,163.
Notice of Allowance issued Feb. 8, 2008 for U.S. Appl. No. 10/523,163.
Examiner Interview Summary Record issued Aug. 2, 2008 for U.S. Appl. No. 10/523,163.
Request for Continued Examination (RCE) with IDS filed May 8, 2008 for U.S. Appl. No. 10/523,163.
Request for Continued Examination (RCE) with IDS filed Oct. 28, 2008 for U.S. Appl. No. 10/523,163.
Amendment filed May 12, 2009 in response to Non-Final Rejection issued Nov. 17, 2008 for U.S. Appl. No. 10/523,163.
U.S. Appl. No. 10/548,716 filed Sep. 8, 2005.
U.S. Appl. No. 10/572,916 filed Nov. 1, 2006.
U.S. Appl. No. 10/577,977 filed Nov. 2, 2004.
Notice of Allowance issued Apr. 21, 2010 for U.S. Appl. No. 10/577,977.
Request for Continued Examination (RCE) with Amendment and IDS filed Jul. 19, 2010 for U.S. Appl. No. 10/577,977.
Notice of Allowance issued Aug. 6, 2010 for U.S. Appl. No. 10/577,977.
Request for Continued Examination (RCE) with Amendment and IDS filed Nov. 8, 2010 for U.S. Appl. No. 10/577,977.
U.S. Appl. No. 10/598,464 filed Mar. 10, 2005.
Non-Final Rejection issued Aug. 6, 2009 for U.S. Appl. No. 10/598,464.
Amendment filed Nov. 3, 2009 in response to Non-Final Rejection issued Aug. 6, 2009 for U.S. Appl. No. 10/598,464.
Non-Final Rejection issued Mar. 1, 2010 for U.S. Appl. No. 10/598,464.
Amendment filed Jun. 1, 2010 in response to Non-Final Rejection issued Mar. 1, 2010 for U.S. Appl. No. 10/598,464.
Non-Final Rejection and claim set for co-pending U.S. Appl. No. 11/911,060 (for obviousness-type double patenting) issued Sep. 3, 2010 for U.S. Appl. No. 10/598,464.
Amendment filed Dec. 14, 2010 in response to Non-Final Rejection issued Sep. 3, 2010 for U.S. Appl. No. 10/598,464.
Ex Parte Quayle Action issued Jan. 25, 2011 for U.S. Appl. No. 10/598,464.
Response to Ex Parte Quayle Action filed Mar. 25, 2011 for U.S. Appl. No. 10/598,464.
Notice of Allowance issued May 26, 2011 for U.S. Appl. No. 10/598,464.

* cited by examiner

FLUID DISPENSING DEVICE

This application is filed pursuant to 35 U.S.C. §371 as a United States National Phase Application of International Patent Application Serial No. PCT/GB2006/001264 filed Apr. 5, 2006, which claims priority from Great Britain Application No. 0507224.4 filed in the United Kingdom on Apr. 9, 2005, the content of which is incorporated herein by reference.

FIELD OF THE INVENTION

The present invention relates to a fluid dispensing device for dispensing a fluid product, for instance a medicament, and is particularly, but not exclusively, concerned with an intra-nasal dispensing device.

BACKGROUND OF THE INVENTION

It is well known to provide a fluid dispenser in which fluid is dispensed via a nozzle or orifice upon the application of a force by a user to a pump dispenser. Such devices are generally arranged with a reservoir containing several doses of a fluid formulation to be dispensed by sequential metered pump actuations. An example of a pump action spray is shown and described in U.S. Pat. No. 4,946,069.

A hand-held, manually operable intra-nasal fluid medicament dispenser is disclosed in WO-A-03/095007, the entire content of which is hereby incorporated herein by reference. The dispenser has a housing which houses a fluid discharge device having a compression pump mounted on a container, which contains the medicament. The housing has at least one finger-operable side lever, which is movable inwardly with respect to the housing to cam the container upwardly in the housing to cause the pump to compress and pump a dose of the medicament out of a pump stem through a nasal nozzle of the housing. In an embodiment shown in FIGS. 19, 19a and 19b, a pair of opposed side levers co-operate with a collar mounted on the neck of the container. The collar provides cam follower surfaces, which ride over cam surfaces of the levers when the levers are moved inwardly. The cam follower surfaces comprise sections, which are inclined at different angles to the direction (axis) of cam movement of the fluid discharge device. The steeper sections provide the dispenser with a commitment feature. In other words, only upon application of at least a minimum finger force to the side levers will the levers be able to overcome the steeper cam follower surface sections. The magnitude of this force, coupled with the change of angle of the cam follower surfaces to the shallower sections, ensures that each lever slides rapidly over the cam follower surfaces once the steeper cam follower surface sections are overcome thereby providing for reliable compression of the compression pump and atomisation of the medicament.

Applicant's co-pending PCT Patent Application no. PCT/GB2005/000944, the entire content of which is hereby incorporated herein by reference, describes another hand-held, manually operable intra-nasal fluid medicament dispenser, in which in a dispensing action, a cam surface of a finger-operable side lever co-operates with a cam follower surface of a collar mounted on the neck of a container to cam the container along an axis to pump fluid medicament therefrom. The cam surface of the lever has a commitment section, oriented at a first angle to the axis, and an adjacent drive section, which is oriented at a second angle to the axis, which is greater than the first angle. In use, the cam follower surface successively rides over the commitment and drive sections of the cam surface. The commitment section thereof is planar.

The Applicant has now found that the interaction of the cam follower surface on the collar with the cam surface of the lever, and hence ease of fluid dispensing, is assisted where the commitment section of the cam surface has an arcuate form. In particular, for smooth actuation of the dispenser it has been found to be beneficial for both the commitment and drive sections to have arcuate forms, wherein those arcuate forms are of opposite arcuate character (e.g. one concave, and the other convex in character).

SUMMARY OF THE INVENTION

According to the present invention there is provided a fluid dispensing device according to claim 1 hereof, and also use of a fluid dispenser.

Useful features of the invention are set forth in the other claims hereof.

The term "finger-operable" means operable by action of the finger or thumb, or combinations thereof, of a typical user (e.g. an adult or child patient).

The term "opposite arcuate character" is used herein to mean (surfaces that) arc in an opposing sense, such as a convex surface that arcs in an opposing sense to a concave surface.

Typically, the minimum actuating force is in the range from 10 to 45N, more typically from 15 to 30N. Such values tend to correspond to a force which presents a suitable 'barrier force' to a weak, nondescript or unintended finger movement whilst readily being overcome by the determined finger (or thumb) action of a user. It will be appreciated that if the device is designed for use by a child or elderly patient it may have a lower minimum actuating force than that designed for adult usage.

Ideally, particularly for medicinal use, the dispenser of the invention dispenses metered doses of the fluid product.

Ideally, the dispenser is configured and arranged to dispense each dose of the fluid product as an atomised spray.

Suitably, the fluid dispenser of the invention incorporates a pump to pump the fluid product dose from the dispenser. The pump may comprise a pre-compression pump, such as the VP3 or VP7 model, or a modified version thereof, manufactured by Valois SA. Typically, such pre-compression pumps are typically used with a bottle (glass or plastic) container capable of holding 8-50 ml of a fluid product. Each actuation will typically deliver 25-150 μl, particularly 50-100 μl, of the fluid product (i.e. a metered dose) and the device is therefore typically capable of providing at least 50 (e.g. 60 or 100) metered doses.

Other suitable dispensing containers include those sold by Erich Pfeiffer GmbH, Rexam-Sofab and Saint-Cobain Calmar GmbH.

For the avoidance of doubt, the various aspects of the invention can be modified to incorporate the other aspects or one or more features of the other aspects.

Further aspects and features of the invention are set forth in the following description of an exemplary embodiment of the invention made with reference to the accompanying drawings.

DETAILED DESCRIPTION OF THE EXEMPLARY EMBODIMENT OF THE INVENTION

FIGS. 1 to 12 show aspects of a fluid dispensing device 1405 for spraying a fluid into a nasal cavity of a human user, which is in accordance with the present invention.

The fluid dispensing device 1405 comprises a plastics housing 1409 (e.g. of ABS), a nozzle 1411 for insertion into the nasal cavity at an upper end of the housing 1409 and a fluid discharge device 1408 housed within the housing 1409 for reciprocal translation along its longitudinal axis X-X. As shown in FIGS. 1 to 5, when the fluid discharge device 1408 is received in the housing 1409, its longitudinal axis X-X is in-line with the nozzle 1411.

The outer surface, or a part of the outer surface, of the nozzle 1411 can be made from a soft-touch plastics material. However, in this embodiment the nozzle 1411 is made from polypropylene (PP).

The fluid discharge device 1408 comprises a container 1430, for storing enough of the fluid for multiple metered doses thereof to be dispensed, and a compression pump 1429 mounted on the container 1430. The container 1430 is made from a translucent or transparent plastics material, although it will be apparent that it could be made from other translucent or transparent materials, such as glass. The pump 1429 has a suction inlet 1461, in the form of a dip tube, located within the container 1430 and a discharge outlet 1463, in the form of a pump stem, for transferring fluid from the pump 1429 to the nozzle 1411.

The housing 1409 is provided with a window 1450 through which the level of the fluid in the container 1430 can be checked.

Pivotally mounted to the housing is a finger operable means 1420 to apply a force to the container 1430 in a direction, which is transverse to the longitudinal axis X-X. This transverse force moves the container 1430 towards the nozzle 1411 along the longitudinal axis X-X so as to actuate the pump 1429. The finger operable means is in the form of a lever 1420 (e.g. of ABS) pivotally connected at its lower end to the housing 1409 and arranged to act upon the container 1430 so as to urge the container 1430 towards the nozzle 1411 when the lever 1420 is pivoted inwardly by a user's finger or thumb.

A protective end cap 1407 is provided for protection of the nozzle 1411. First and second lugs 1449a, 1449b project from the protective end cap 1407 for receipt within suitably arranged channels 1451a, 1451b provided within the housing 1409 such as to allow secure attachment of the end cap 1407 to the housing 1409. When so-received, first lug 1449a further interferes with movement of lever 1420 such as to prevent actuation (i.e. to lock movement) of the lever 1420 when the end cap 1407 and lugs 1449a, 1449b are in place (i.e. in the nozzle covered position).

The end cap 1407 also has a protruding stopper 1460 which has a convex, resilient end form 1461 arranged for sealing engagement with the dispensing orifice 1415 of the nozzle 1411 so as provide an essentially airtight seal to nozzle orifice 1415 to prevent fluid drain back when the stopper 1460 is in place.

The end cap is suitably made from the same material as the housing, e.g. a plastics material, suitably ABS.

As will be understood by reference to FIGS. 3, 5, 7A and 10, the lever 1420 has a pair of beaks or noses 1421, each of which presents a cam surface 1422 arranged for interaction with one of a pair of cam follower surfaces 1492 provided on a collar 1490 (e.g. of acetal) fixed around the neck of the container 1430. It will be appreciated that a sideways force (i.e. substantially transversely to the longitudinal axis X-X of the fluid discharge device 1408) applied to the lever 1420 results in the cam follower surfaces 1492 riding over the cam surfaces 1422 thereby resulting in upward movement (i.e. along the longitudinal axis X-X) of the fluid discharge device 1408.

Figure 7A:
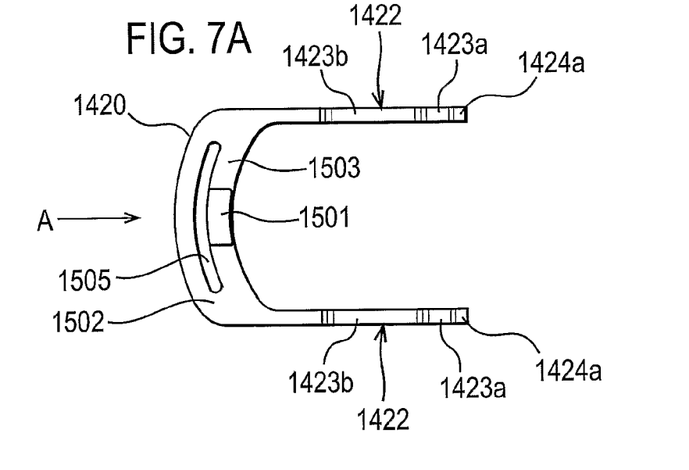
FIG. 7A is a schematic plan view of an actuator lever of the fluid dispensing device.
Figure 7B:
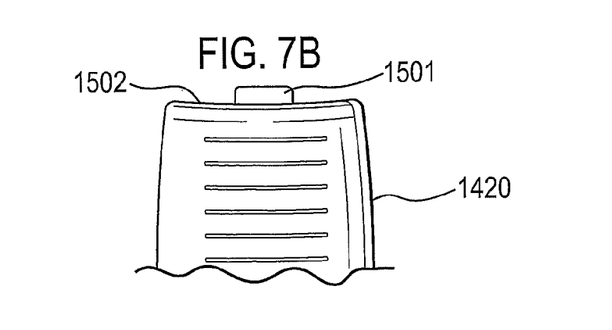
FIG. 7B is a side view of the lever taken on arrow A in FIG. 7A.

In more detail, the beaks 1421 are located at the upper end of the lever 1420 on opposite sides thereof. In plan view, the upper end of the lever 1420 has a U-shaped cross section, as shown in FIG. 7A. The beaks 1421 straddle opposed sides of the fluid discharge device 1408 for co-operation with the diametrically opposed cam follower surfaces 1492 on the collar 1490. Noting that the fluid dispensing device 1405 only has one actuator lever 1420, the use of a pair of beaks 1421 improves the ability of the lever 1420 to cam the fluid discharge device 1408 upwardly along its longitudinal axis X-X.

Each cam surface 1422 of the lever 1420 has a variable mechanical ratio arranged such that until a pre-determined force is applied to the lever 1420 no significant force is transferred to the container 1430. In more detail, each cam surface 1422 has a commitment portion 1423a which is inclined at a first angle to the longitudinal axis X-X of the fluid discharge device 1408 and a drive portion 1423b inclined to the longitudinal axis X-X at a second angle, which is greater than the first angle. The first angle should be no less than approximately 20°, and is suitably in the range of approximately 20-35°, more suitably approx. 20-26°, even more suitably approx. 22-26°. The second angle may be in the range of approximately 40-60°, suitably approx. 40-50°, more suitably approx. 45°.

Therefore, when an inward force is initially applied to the lever 1420 it is applied substantially normally to the longitudinal axis X-X of the fluid discharge device 1408 and virtually no force is converted into a force along the longitudinal axis X-X of the fluid discharge device 1408 and so the static friction between the commitment portions 1423a of the beaks 1421 and the cam follower surfaces 1492 is sufficient to maintain the lever 1420 effectively stationary. However, when a pre-determined load is applied to the lever 1420 the static friction is overcome and the cam follower surfaces 1492 start riding on the commitment portions 1423a.

When the cam follower surfaces 1492 reach the end of the commitment portions 1423a, the increase in inclination of the cam surfaces to the longitudinal axis X-X in combination with the magnitude of the force being applied ensures that the cam follower surfaces 1490 suddenly slide rapidly along the drive portions 1423*b* causing the container 1430 to be moved rapidly towards the nozzle 1411 to actuate the compression pump. This ensures that the pump is only actuated when sufficient force is being applied to guarantee the production of an effective spray from the nozzle 1411.

Figure 10:
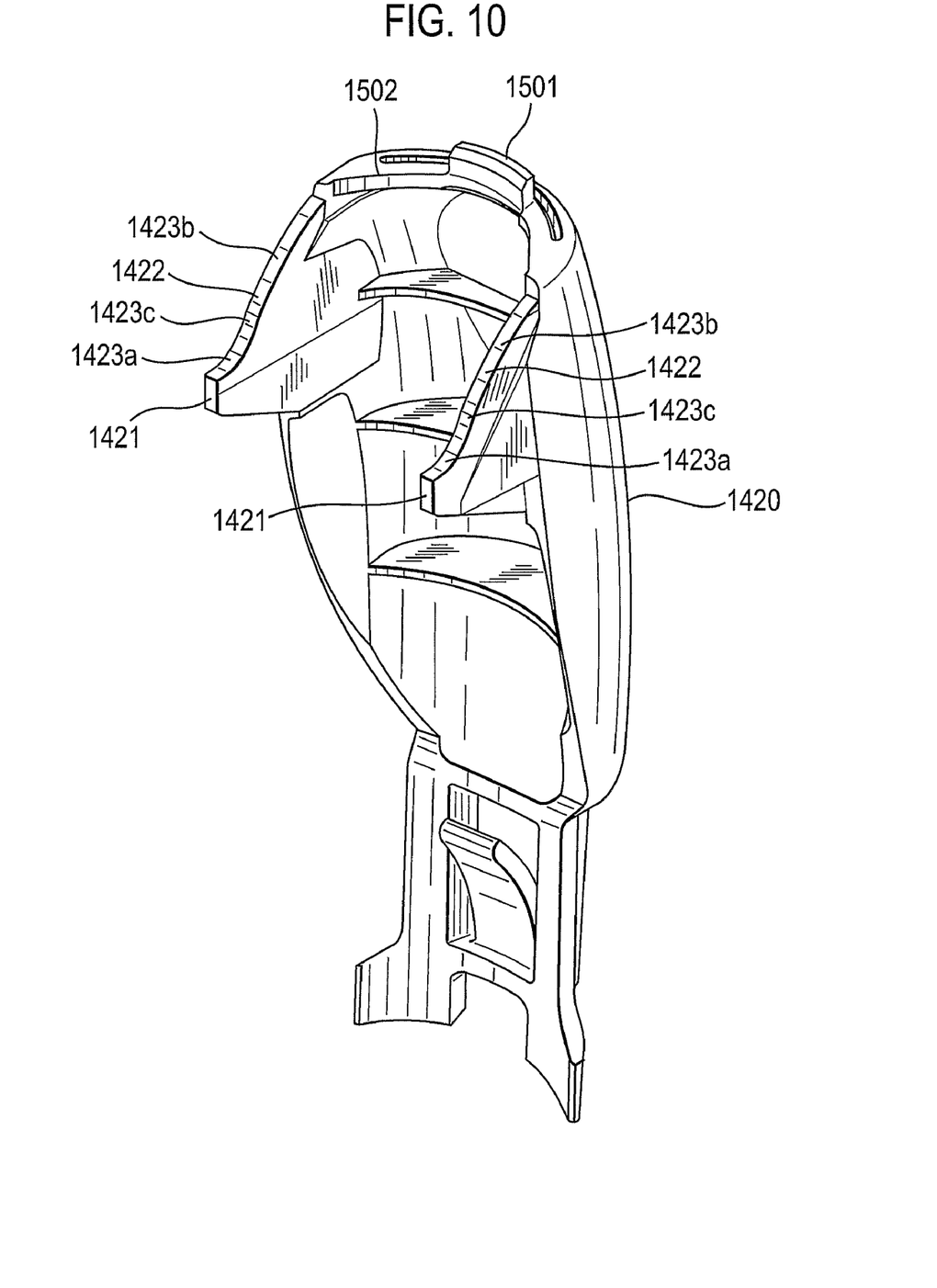
FIG. 10 is a perspective view of an actuator lever of the fluid dispensing device.
Figure 11:
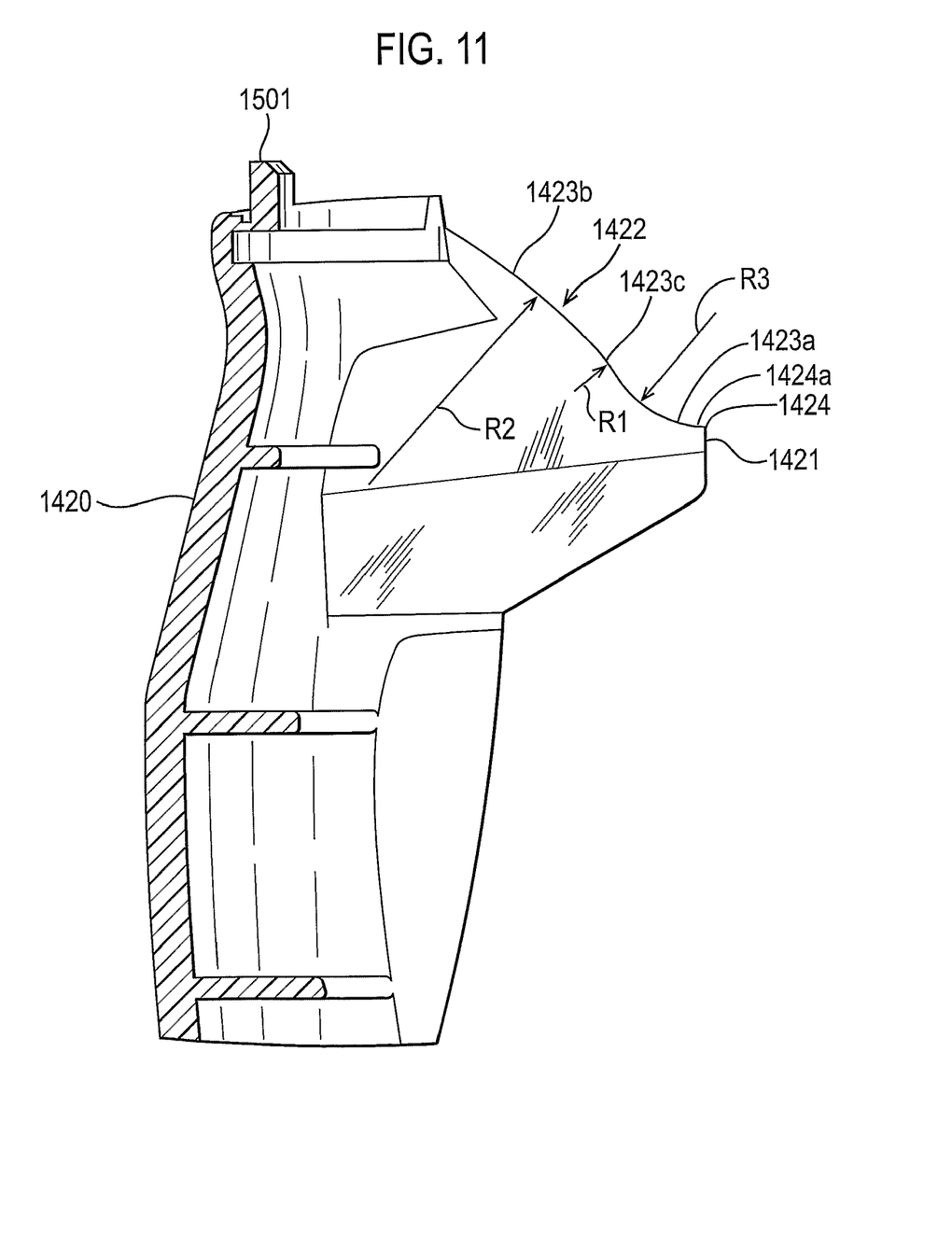
FIG. 11 is a section view of an actuator lever of the fluid dispensing device.

Referring mainly to FIGS. 10 and 11, it will be seen that the commitment sections 1423*a* are arcuate and arranged to present a concavely arcuate surface to the cam follower surfaces 1490. The drive sections 1423*b* are also arcuate and arranged to present a convexly arcuate surface to the cam follower surface 1490.

More specifically, and with particular reference to FIG. 11, the drive portions 1423*b* have a short rounded transition section 1423*c* contiguous with the associated commitment portion 1423*a*. The transition sections 1423*c* have a radius of curvature R1 that is lesser than the radius of curvature R2 of the remainder of the drive portion 1423*b*, which radius R2 is constant over the length of the remainder of the drive portion 1423*b*. The transition portions 1423*c* smooth the transfer of the cam follower surfaces 1429 from the commitment portions 1423*a* of the cam surfaces 1422 to the drive portions 1423*b*. They also reduce wearing of the cam surfaces 1422. As shown, the radius of curvature R3 of the commitment section 1423*a* is greater than that of R1 but less than that of R2.

R1 in this embodiment is about 3 mm, while R2 is about 25 mm and R3 about 10 mm. Nonetheless, other radii could be used, as will be appreciated by the skilled person in the art.

Figure 3:
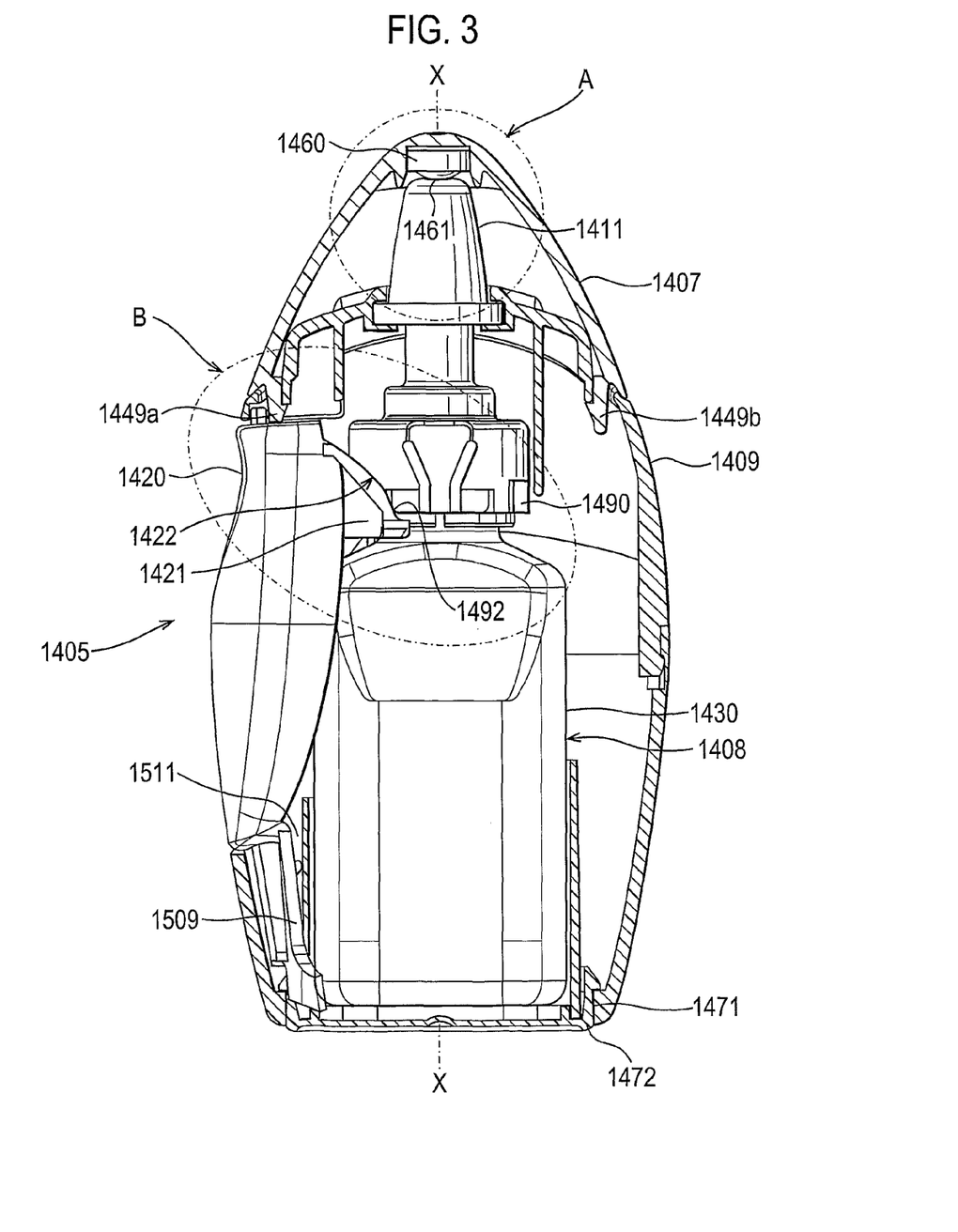
FIG. 3 is a partial longitudinal sectional view of the dispenser.
Figure 4:
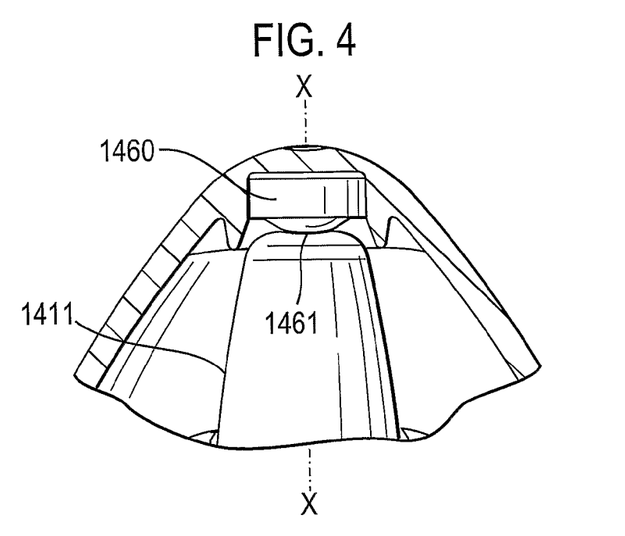
FIG. 4 is an enlarged view of area A in FIG. 3.

Referring to FIG. 3, the cam follower surfaces 1492 are rounded edges of diametrically opposed embossments 1493 on the plastic collar 1490. This makes riding of the cam follower surfaces 1492 on the cam surfaces 1422 easier, and also reduces wearing of the respective surfaces.

Figure 5:
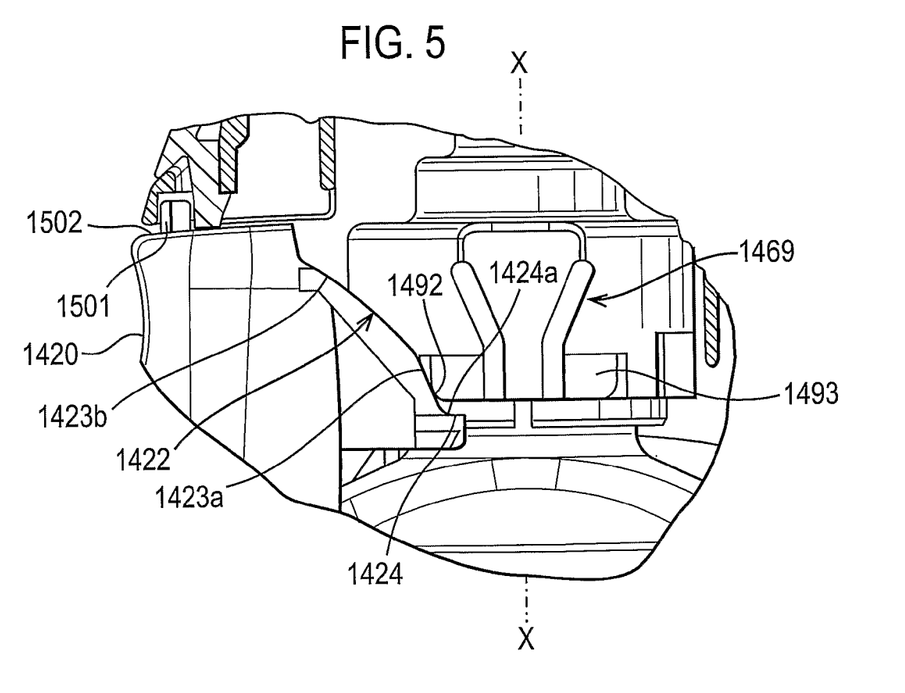
FIG. 5 is an enlarged view of area B in FIG. 3.

As shown most clearly in FIGS. 5 and 11, the beaks 1421 have a tip, which forms a cradle 1424 for the embossments 1493 on the collar 1490 of the fluid discharge device 1408 to rest on. The cradles 1424 present a support surface 1424*a*, which extends transversely to the longitudinal axis X-X on which the embossments 1493 can be supported. The cradles 1424 act as a back-stop for the fluid discharge device 1408 insofar as preventing the fluid discharge device 1408 moving downwardly beyond the point at which the cradles 1424 engage with the embossments 1493. As will be seen from FIG. 5, this ensures that the cam follower surfaces 1492 are aligned with the commitment portion 1423*a* of the cam surfaces 1422.

Noting that the lever 1420 pivots inwardly, it will be appreciated that as the lever 1420 pivots inwardly the inclined angle which the planar commitment portions 1423*a* make with the longitudinal axis X-X becomes smaller (steeper) thereby increasing the resistance of the fluid discharge device 1408 to being cammed upwardly.

However, the arcuate nature of the drive portions 1423*b*, in particular that part after the transition section 1423*c*, is such that the inclined angle it makes with the longitudinal axis X-X remains the same, or substantially the same, as the lever 1420 pivots inwardly. More specifically, consider that as the lever 1420 pivots inwardly the point on the section of the drive portion 1423*b* having the radius of curvature R2, which is in contact with the cam follower surface 1492, moves up the cam surface 1422. The angle that a tangent to this changing contact point makes with the longitudinal axis X-X remains the same, or substantially the same, as the lever 1420 pivots inwardly to cause the fluid discharge device 1408 to spray a metered dose of the fluid product from the nozzle 1411. This feature means that the resistance to the inward movement of the lever 1420 never increases after the commitment feature has been overcome, as would be the case if the drive portion 1423*b* were a planar surface since its angle to the longitudinal axis X-X would then increase as the lever 1420 pivots inwardly.

The aforementioned features of the cam profile mean that the operator receives smooth tactile feedback from the device 1405 when the lever 1420 is actuated to cause the fluid discharge device 1408 to spray a metered dose of the fluid product from the nozzle 1411.

To use the fluid dispensing device 1405 a user first has to remove the protective cap 1407 thereby unsealing the nozzle orifice 1415 by removing the stopper end 1460 therefrom. The user then grasps the fluid dispensing device 1405 and places a thumb and/or finger on the lever 1420.

Provided that only a light pressure is applied to the lever 1420 no fluid will be discharged and the user is able to manoeuvre the dispensing nozzle 1411 of the fluid dispensing device 1405 into one of their nostrils so that the fluid can be dispensed into the nasal cavity.

If the user then squeezes the lever 1420 inwards with increasing force the threshold force defined by the interaction of the cam follower surfaces 1492 with the commitment portions 1423*a* of the cam surfaces 1422 is overcome resulting in the container 1430 being moved rapidly towards the nozzle 1411 to actuate the pump 1429 and dispense fluid to the dispensing orifice 1415. Upon release of the pressure applied to the lever 1420 the pump is reset by its internal return spring. Moreover, the lever 1420 has a leaf spring 1465 (FIG. 2), which acts against a housing inner wall 1467 to bias the lever 1420 to its rest position shown in FIGS. 1 to 3 and 5.

The actuating procedure can then be repeated until all of the fluid in the container 1430 has been used. However, only one or two doses of fluid are normally administered at a time.

Figure 9:
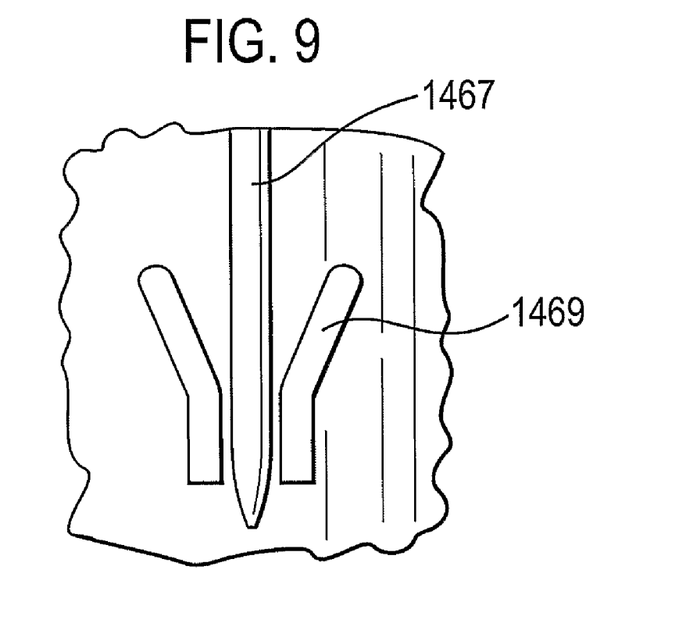
FIG. 9 is a schematic representation of a guide mechanism of the fluid dispensing device.

Referring to FIGS. 5 and 9, to counteract the lateral force which the lever 1420 applies to the fluid discharge device 1408, and to guide the axial displacement of the fluid discharge device 1408 in response to the lever operation, the collar 1490 has a pair of diametrically opposed, tracks 1469 which are arranged parallel to the longitudinal axis X-X. These tracks 1469 are provided by the embossments 1493. Each track 1469 has a funnel shape at its upper end for self-guiding of the tracks 1469 onto complementary axially-extending runners 1467, presented on the inner surface of the housing 1409, when the fluid discharge device 1408 is inserted into the housing 1409 through an (lower) opening 1471 in its lower end, which lower opening 1471 is subsequently closed with a cap 1472. It will also be appreciated that the track-runner mechanism positions the collar 1490 in the correct angular orientation about the longitudinal axis X-X so that the cam follower surfaces 1492 face the cam surfaces 1422.

In use, the tracks 1469 ride on the runners 1467 when the lever 1420 overcomes the threshold force provided by the commitment portions 1423*a* of the cam surfaces 1422. As will be appreciated, the co-operation of the tracks 1469 with the runners 1467 prevents rotation of the collar 1490 in the housing 1409.

Figure 2:
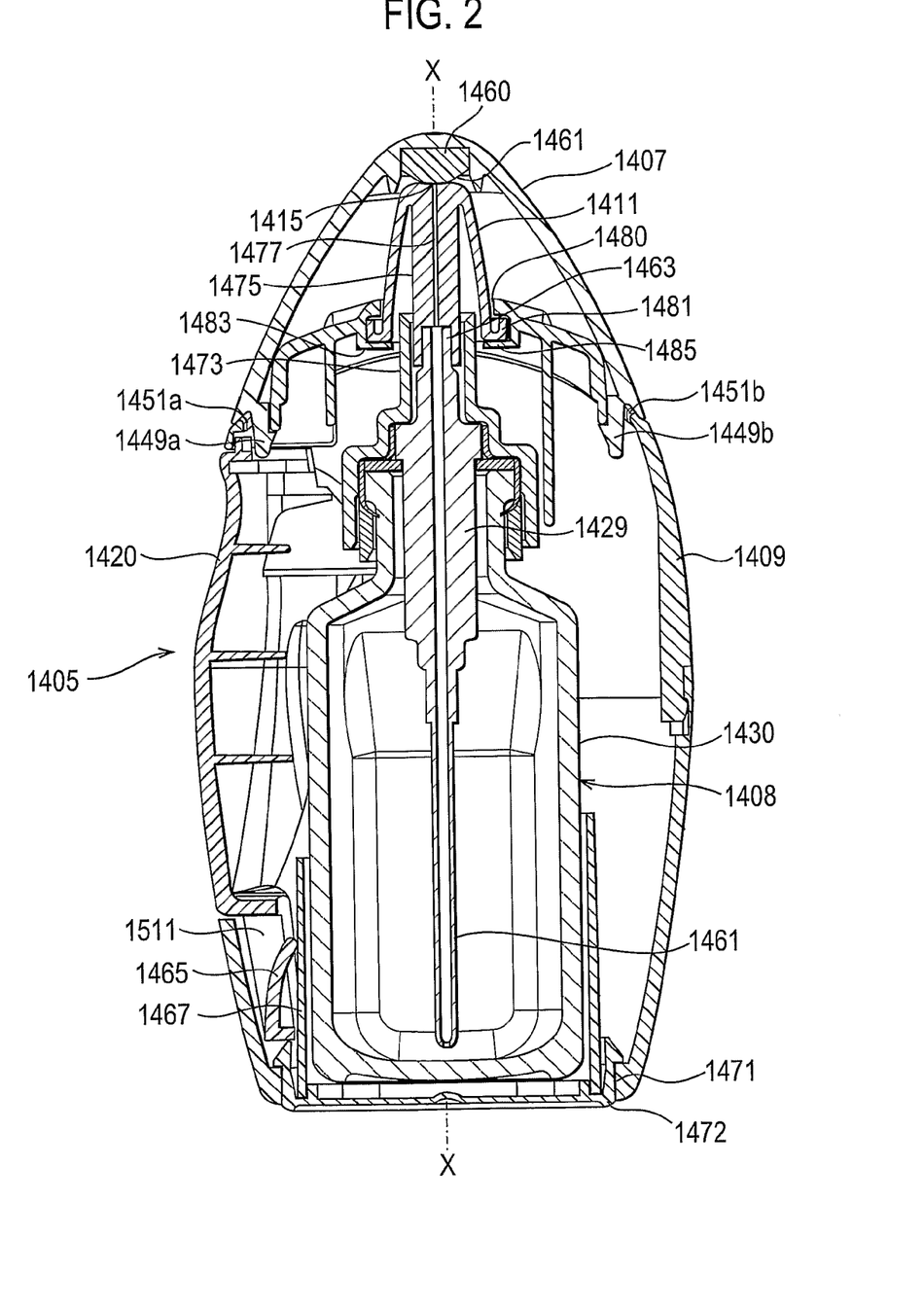
FIG. 2 is a longitudinal sectional view of the dispenser.

In addition to the tracks 1469, the collar also has a sheath 1473 for the pump stem 1463, which forms a sliding fit on an inner hollow post 1475 of the nozzle 1411 in which a nozzle outlet passage 1477 is formed. As shown in FIG. 2, the pump stem 1463 is located in a lower widened portion of the outlet passageway 1477 through an interference fit. It will therefore be appreciated that the pump stem 1463 remains stationary in the housing 1409 as the container 1430 and the collar 1490 are translated upwardly by the lever 1420, i.e. there is relative movement between the container-collar unit and the pump stem. In this way, the pump 1429 is compressed and a metered dose of the fluid product discharged through the pump stem 1463 into the outlet passageway 1477 for ejection from the nozzle orifice 1415 at the end of the outlet passageway 1477. The commitment feature on the lever 1420 ensures that the pumping force is sufficient for atomisation of the fluid product from the nozzle 1411.

Figure 8:
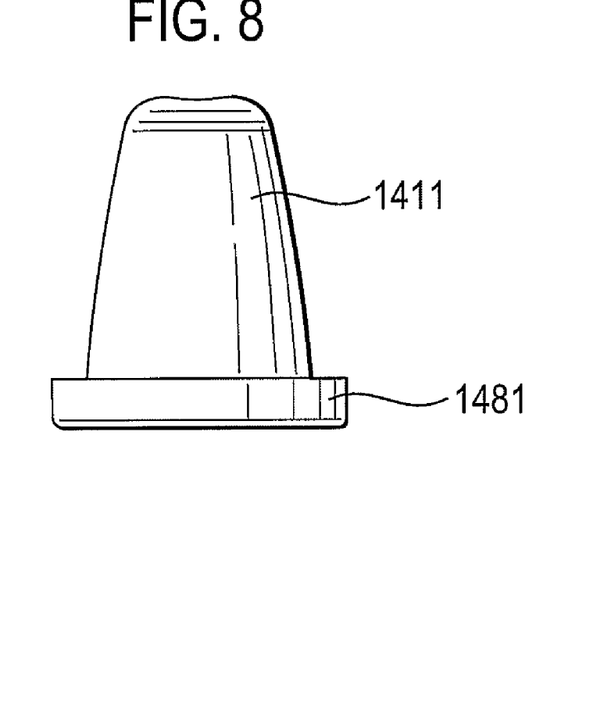
FIG. 8 is a side view of the nozzle.

As shown in FIG. 8, the nozzle 1411 in this embodiment is formed as a separate part from the housing 1409. This has advantages when the fluid product being dispensed is a medicament because this isolates the only part of the device that comes into contact with the medicament. Accordingly, testing of the pharmaceutical performance of the nozzle 1411 can be conducted without the need for the housing 1409. So, once the nozzle 1411 is complete, testing of it can begin while the development and design of the housing 1409 continues. Therefore there is no hold up in the device development, as would be the case if the nozzle 1411 were integrally formed with the housing 1409. Any change in the moulding of the housing would require re-testing of the nozzle 1411 to confirm that the new moulding has had no adverse effect on the nozzle performance.

In addition, having a separate nozzle 1411 means that the housing 1409 can be customised for different markets and/or different products. As an example, the nozzle 1411 could be a universal nozzle for a set of housings having different shapes, different colours, etc.

A further advantage of a separate nozzle 1411 is that it can be more easily formed from a different material than the housing 1409, for example one that is more acceptable for insertion into a nostril and/or for contacting the fluid product, especially where this is a medicament, but which might be too expensive to form the whole housing 1409 from.

Figure 6:
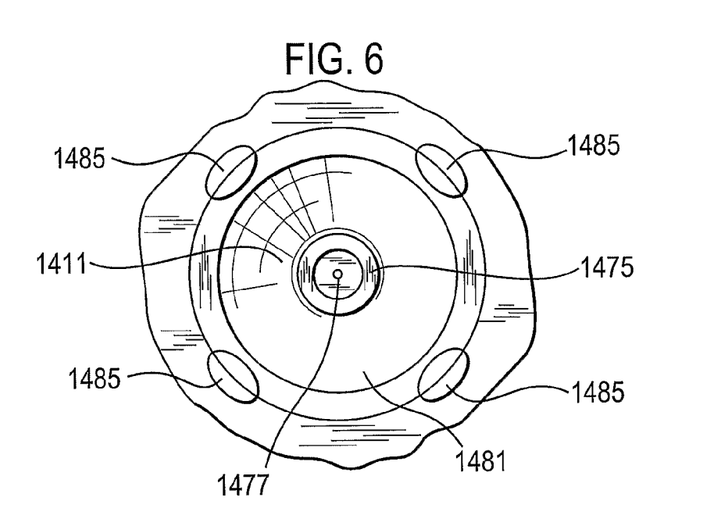
FIG. 6 is a fragmentary, enlarged underneath plan view of a nozzle of the fluid dispensing device mounted in a housing of the device.

To this end, and as shown in FIG. 2, the housing 1409 has an (upper) opening 1480 at its upper end through which the nozzle 1411 is insertable. Referring to FIGS. 2, 6 and 8, the nozzle 1411 has a flange 1481 at its lower end which engages the inner mouth of the upper opening 1480 so that the tip of the nozzle 1411 projects from the upper opening 1480 the required distance for nasal use. As will be seen from FIGS. 2 and 6, the inner mouth of the upper opening 1480 is bounded by a collar 1483 formed from a series of collar segments 1485 angularly spaced-apart about the longitudinal axis X-X. The collar segments 1485 are bent over the nozzle flange 1481 by a swaging tool to clamp the nozzle flange 1481 against the inner mouth to fix the nozzle 1411 in the upper opening 1480.

Figure 1:
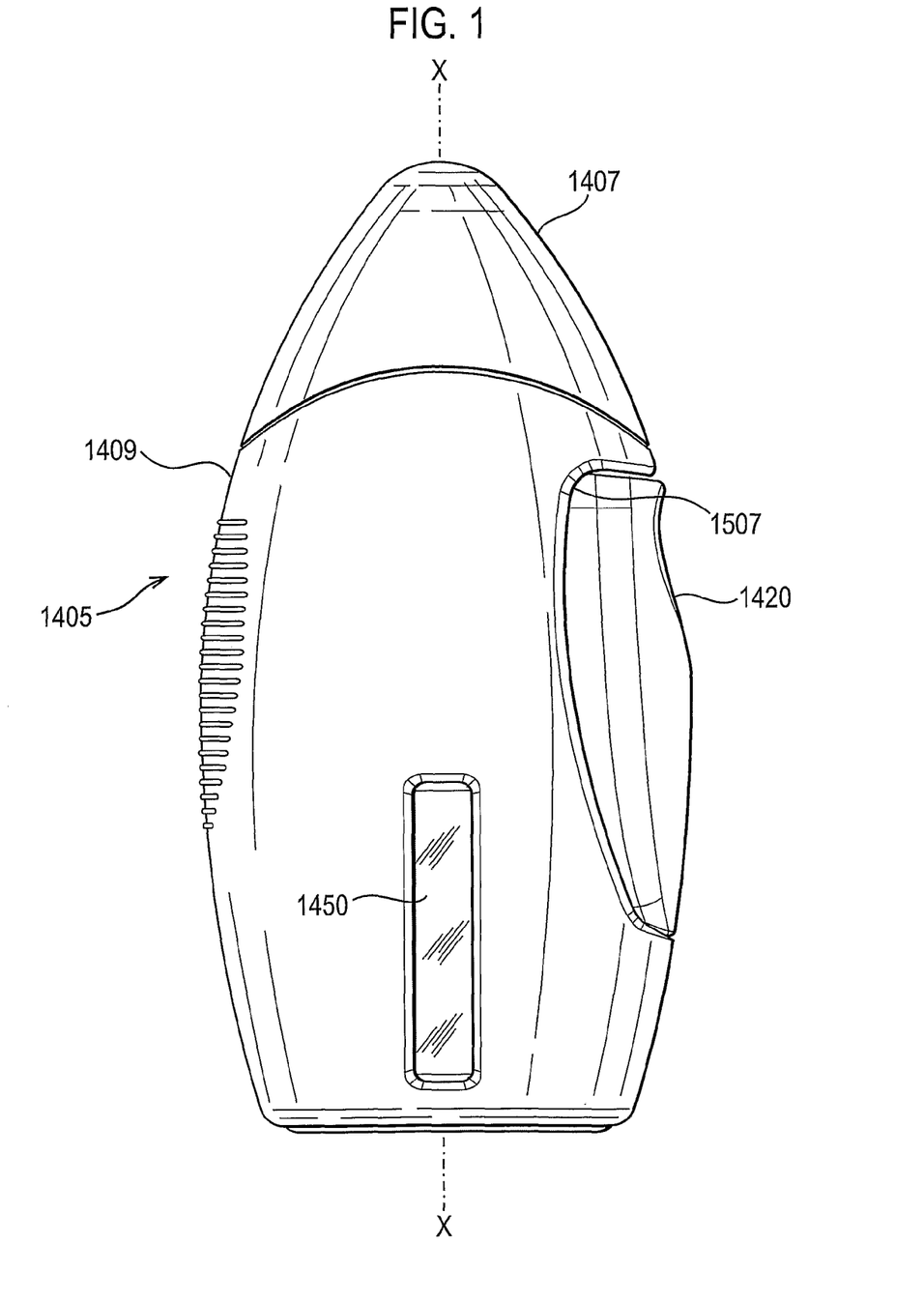
FIG. 1 is a side view of a fluid dispensing device of the invention.

To assist in assembly of the fluid dispensing device 1405, the lever 1420 is provided with means to enable it to be disposed in an outward position with respect to the housing 1409, to allow the fluid discharge device 1408 to be inserted into the housing 1409 through the lower opening 1471 to its rest position shown in FIGS. 1, 3 and 5, and the inward position with respect to the housing 1409 shown in FIGS. 1 to 3.

Referring to FIGS. 7A, 7B, 10, 11 and 12, at the upper end of the lever 1420 there is provided a tab 1501 which projects above the upper edge 1502 of the lever 1420. The tab 1501 projects from a resilient bridge element 1503 formed by a cutout 1505 in the lever 1420. The resilient bridge element 1503 biases the tab 1501 to its extended position, but enables the tab 1501 to be depressed so that it is flush with, or below, the lever upper edge 1502.

As will be understood from FIG. 1, the lever 1420 is mounted in a slot 1507 formed in the side of the housing 1409.

Figure 12:
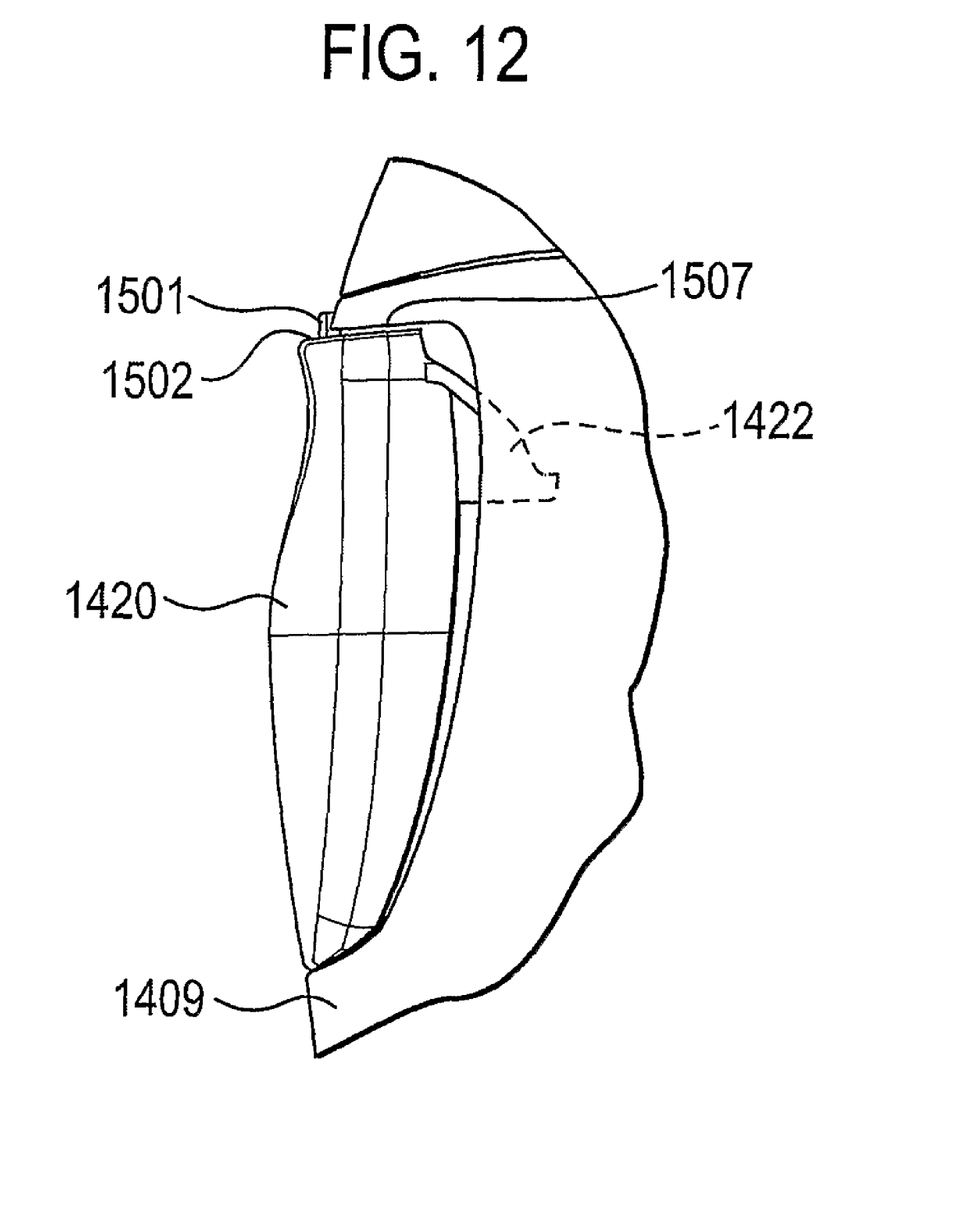
FIG. 12 is a fragmentary, schematic view of the lever in an outward position relative to the housing of the fluid dispensing device.

The lever 1420, which is formed separately from the housing 1409, but from the same plastics material, is mounted to the housing by first inserting its lower end 1509, which carries the leaf spring 1465, through the slot 1507 to be received in an axial channel 1511. The lever 1420 is now disposed in its outward position with the tab 1501 bearing against the edge of the slot 1507 to prevent the lever 1420 being moved through the slot 1507 to its inward position, as schematically shown in FIG. 12.

When the lever 1420 is in its outward position, the fluid discharge device 1408 is able to be inserted into the housing 1409 through the lower housing opening 1471 to its rest position because the lever 1420, and its beaks 1422 in particular, do not impede the loading of the fluid discharge device 1408.

After the fluid discharge device 1408 has been loaded to its rest position, the lever 1420 is moved to its inward position by depressing the tab 1501 so that it clears the edge of the slot 1507 and then pushing the lever 1420 inwardly to its position shown in FIG. 2, for example. If the lever 1420 were in its inward position before the fluid discharge device 1408 were loaded into the housing 1409, the fluid discharge device could not be loaded into the housing 1409 to its rest position, not without damaging the lever 1420 in any event.

As shown in FIG. 2, for example, once the lever 1420 is moved to its inward position, the tab 1501 returns to its extended position and bears against an inner surface of the housing 1409 to maintain the lever 1420 in the inward position. In this regard, the lever leaf spring 1465 biases the lever 1420 outwardly.

In more detail, the tab 1501 bears against an inner surface of one of the channels 1451a in the housing 1409 in which the cap lugs 1449a, 1449b are snap-fitted to hold the protective cap 1407 releasably captive on the housing 1409. As shown in FIG. 2, the lug 1449a received in the channel 1451a is located in front of the tab 1501. It will therefore be gathered that the lever 1420 is prevented from moving inwardly when the cap 1407 is in place, to actuate the fluid dispensing device 1405, by the lug 1449a blocking inward movement of the lever tab 1501.

Those parts of the fluid dispensing device 1405 made from a plastics material are formed by a moulding process.

Other features of this exemplary embodiment are contained in the other sections of this specification, including, without limitation, the appended claims and statements in the 'Summary of the Invention' section supra.

The fluid discharge device 1408 may contain a medicament formulation, for example for the treatment of mild, moderate or severe acute or chronic symptoms or for prophylactic treatment. The precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

Appropriate medicaments may be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α, 9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is formulated as any suitable fluid formulation, particularly a solution (e.g. aqueous) formulation or a suspension formulation, optionally containing other pharmaceutically acceptable additive components.

Suitably, the fluid medicament formulation herein has a viscosity of from 10 to 2000 mPa·s (10 to 2000 centipoise), particularly from 20 to 1000 mPa·s (20 to 1000 centipoise), such as from 50 to 1000 mPa·s (50 to 1000 centipoise) at 25° C.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are non-toxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semi-synthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Suitable solution formulations may comprise a solubilising agent such as a surfactant. Suitable surfactants include α-[4-(1,1,3,3-tetramethylbutyl)phenyl]-ω-hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate medicament and optionally suspending agents, preservatives, wetting agents or isotonicity adjusting agents.

The particulate medicament suitably has a mass mean diameter (MMD) of less than 20 μm, preferably between 0.5-10 μm, especially between 1-5 μm. If particle size reduction is necessary, this may be achieved by techniques such as micronisation and/or microfluidisation.

Suitable suspending agents include carboxymethylcellulose, veegum, tragacanth, bentonite, methylcellulose and polyethylene glycols.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 μg, 50 μg, 100 μg, 200 μg or 250 μg of active medicament. The precise dosage is either known or readily ascertainable by those skilled in the art.

It will be understood that the present disclosure is for the purpose of illustration only and the invention extends to modifications, variations and improvements thereto.

All usage herein of terms such as "about", "approximately", "substantially" and the like in relation to a parameter or property is meant to include the exact parameter or property as well as immaterial deviations therefrom.

The invention claimed is:

1. A fluid dispensing device for dispensing a fluid product having:
   a dispensing outlet from which the fluid product is dispensable,
   a supply of the fluid product,
   a dispensing member mounted for movement in a dispensing direction along an axis from a first position to a second position which causes a dose of the fluid product in the supply to be dispensed from the dispensing outlet, and
   a finger-operable actuator member mounted for movement in an actuating direction which is generally transverse to the axis,
   wherein the actuator member has at least one cam surface and the dispensing member has at least one cam follower surface,
   wherein the actuator member is movable in the actuating direction to cause the at least one cam surface to bear against the at least one cam follower surface to force the at least one cam follower surface to ride on the cam surface to cam the dispensing member in the dispensing direction from the first position to the second position,
   wherein the at least one cam surface has a concavely arcuate commitment section, and an adjacent convexly arcuate drive section, wherein the concavely arcuate section and the convexly arcuate section define a continuously curved cam surface such that the entire cam surface is continuously curved,
   wherein the device is configured and arranged such that, in use, the at least one cam follower surface successively rides on the commitment and drive sections of the at least one cam surface, on movement of the actuator member in the actuating direction, to cam the dispensing member from the first position to the second position, and
   wherein the commitment section is constructed such that a minimum actuating force is required to be applied to the actuator member to cause the at least one cam follower surface to ride on the commitment section onto the drive section.

2. The device of claim 1, wherein the commitment section has a radius of curvature in the range of about 5-20 mm.

3. The device of claim 1, wherein the drive section has an arcuate transition sub-section contiguous with the commitment section.

4. The device of claim 3, wherein the transition sub-section has a radius of curvature in the range of about 1-5 mm.

5. The device of claim 3, wherein the arcuate transition sub-section of the drive section has a first radius of curvature and a remainder of the drive section has a second radius of curvature that is greater than the first radius of curvature.

6. The device of claim 5, wherein the first arcuate portion has a radius of curvature in the range of about 1-5 mm and the second arcuate portion has a radius of curvature in the range of about 15-40 mm.

7. The device of claim 1, wherein the minimum actuating force is in the range of about 10-45 N.

8. The device of claim 1, wherein the actuator member is mounted in the device for movement on an arcuate path in the actuating direction.

9. The device of claim 1, wherein, in use, the at least one cam surface bears against the at least one cam follower surface at a contact point on the at least one cam surface, a tangent to the contact point forms an angle to the axis, and the device is configured and arranged such that when the contact point is on the drive section of the cam surface, the angle to the axis remains constant, or substantially constant, as the actuator member moves in the actuating direction.

10. The device of claim 1, wherein the actuator member is mounted for pivotal movement about a first end thereof and the at least one cam surface is disposed on the actuator member remote from the first end.

11. The device of claim 1, wherein the dispensing member is a dispensing container in which the supply of the fluid product is contained.

12. The device of claim 10, wherein the dispensing direction is an upward direction and the first end of the actuator member is a lower end thereof.

13. The device of claim 12, wherein the at least one cam follower surface is disposed towards an upper end of the dispensing member.

14. The device of claim 11, wherein the dispensing container has a pump which is caused to pump the dose of the fluid product from the dispensing outlet in response to the dispensing container being moved in the dispensing direction by the actuator member.

15. The device of claim 1, wherein the dispensing outlet is in a nozzle sized and shaped for insertion into a nostril of a human body.

16. The device of claim 1, wherein the supply contains a volume of fluid medicament formulation.

17. A fluid dispensing device for dispensing a fluid product comprising;
a housing,
a dispensing member mounted within the housing, for movement in a dispensing direction along an axis from a first position to a second position,
a finger operable actuator member moveably mounted to the housing, for movement in an actuating direction,
wherein the finger operable actuator member has at least one cam surface and the dispensing member has at least one cam follower surface,
wherein the at least one cam surface is a continuously curved surface comprising a first surface of concave constant radius, an adjoining second surface of constant convex radius, and an adjoining third surface of constant convex radius,
and the at least one cam follower surface is adapted to ride sequentially on the first surface, onto the second surface, on the second surface onto the third surface, and on the third surface, such that actuation of the lever causes the dispensing member to move from the first position to the second position,
wherein the actuating member and actuator member are adapted such that a threshold force must be applied to the finger operable actuator member to enable movement of the at least one cam follower surface sequentially on the first surface onto the second surface, on the second surface onto the third surface.

18. A fluid dispensing device as claimed in claim 17 wherein the third convex surface has a radius of curvature greater than the second convex surface.

19. A fluid dispensing device as claimed in claim 17 wherein the cam follower surface is rounded.

20. A fluid dispensing device as claimed in claim 17 wherein the at least one cam surface defines an s-shaped curve.

* * * * *